United States Patent [19]

DeWoskin

[11] 4,375,962
[45] Mar. 8, 1983

[54] ORTHODONTIC TRACTION APPARATUS

[75] Inventor: Irvin S. DeWoskin, St. Louis County, Mo.

[73] Assignee: Orthoband Company, Inc., Barnhart, Mo.

[21] Appl. No.: 317,479

[22] Filed: Nov. 2, 1981

[51] Int. Cl.³ .............................................. A61C 7/00
[52] U.S. Cl. ...................................................... 433/5
[58] Field of Search ............................................ 433/5

[56] References Cited

FOREIGN PATENT DOCUMENTS 2803560 2/1979 Fed. Rep. of Germany .......... 433/5

*Primary Examiner*—Robert Peshock
*Attorney, Agent, or Firm*—Senniger, Powers, Leavitt and Roedel

[57] ABSTRACT

Orthodontic traction apparatus adapted for attachment, via elastic bands or the like, to an orthodontic instrumentality associated with the teeth for applying traction to the teeth generally in the forward direction with respect to the head. The apparatus comprises headgear adapted to be worn on the head, and a relatively rigid chin cup adapted for connection to the headgear. An implement in the form of a wire arm extends up from the chin cup for attachment at its upper end, via the elastic bands, to the orthodontic instrumentality. The arm is mounted on the chin cup for movement in the direction of its longitudinal axis for adjustment of the position of the upper end of the arm relative to the mouth and for movement relative to the chin cup generally in side-to-side direction with respect to the head.

12 Claims, 4 Drawing Figures

ORTHODONTIC TRACTION APPARATUS

BACKGROUND OF THE INVENTION

This invention relates to orthodontic apparatus, and more particularly to orthodontic traction apparatus for applying traction to a patient's teeth in the anterior or forward direction with respect to the head.

Various types of orthodontic traction apparatus are used in connection with so-called reverse-pull extra-oral traction procedures in which traction is applied to a patient's teeth in the anterior or forward direction via elastic bands attached to an orthodontic instrumentality on the teeth. Typically, these types of apparatus are classified with reference to the direction in which they apply traction force to the teeth. High-pull traction apparatus, for example, applies traction along a line extending upwardly from the teeth to a point of attachment for the elastic bands on the apparatus forward and above the patient's mouth. Such apparatus is useful in the treatment of orthodontic deficiencies of the maxilla. In contrast, low-pull traction apparatus applies traction along a line extending downwardly from the teeth to a point of attachment on the apparatus forward and below the patient's mouth and is useful in the treatment of orthodontic deficiencies of the mandible. Because the prior art traction apparatus, in most instances, lacks a feature enabling adjustment of the position of the points of attachment relative to the patient's mouth, such apparatus is typically useful only in the treatment of the orthodontic deficiency for which it was specifically designed and not in the treatment of other orthodontic deficiencies. Consequently, a relatively large number of different types of orthodontic traction apparatus must be manufactured and maintained in inventory, thereby adding to the cost of such apparatus.

SUMMARY OF THE INVENTION

Among the several objects of the invention may be noted the provision of an improved orthodontic traction apparatus useful in reverse-pull extra-oral traction procedures which has an adjustability feature enabling its use in the treatment of a number of different orthodontic deficiencies; the provision of such apparatus in which the position of the points of attachment it provides for the elastic bands may readily be adjusted both vertically with respect to the patient's mouth and from side-to-side with respect to the patient's head; and the provision of such apparatus which may be readily fitted on the patient's head, is comfortable to wear for extended periods of time, and is of economical and durable construction.

In general, apparatus of this invention comprises headgear adapted to be worn on the head, and a relatively rigid chin cup having a central section shaped to conform to the contour of the chin and end sections adapted for connection to said headgear. It further comprises an implement in the form of a wire arm on the central section of the chin cup adapted to extend up from the chin cup for attachment at its upper end, via elastic bands or the like, to an instrumentality or instrumentalities associated with the teeth for applying traction to the teeth generally in the forward direction with respect to the teeth. Means mounts the arm on the chip cup for movement in the direction of its longitudinal axis for adjustment of the position of the upper end of the arm relative to the mouth and for movement relative to the chin cup generally in side-to-side direction relative to the head. Means associated with the mounting means secures the arm in various positions of adjustment.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
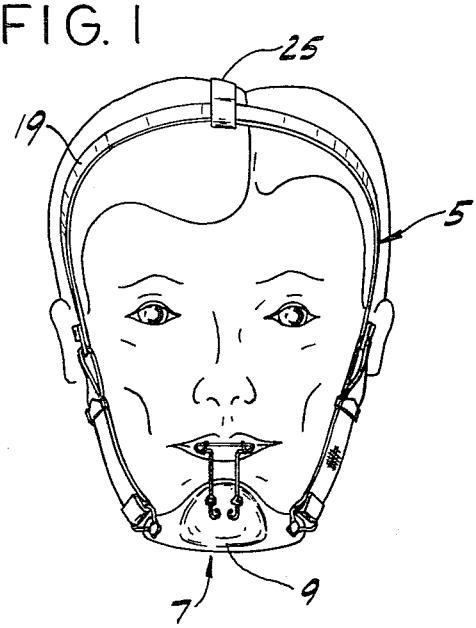
FIG. 1 is a front elevation of orthodontic traction apparatus of this invention as worn on a patient's head.
Figure 2:
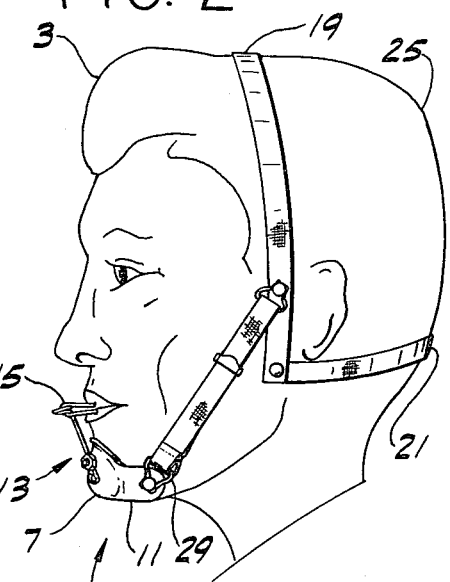
FIG. 2 is a left side elevation of FIG. 1.

Referring to the drawings, and more particularly to FIGS. 1 and 2, there is generally indicated at 1 orthodontic traction apparatus of this invention as worn on a patient's head 3. The apparatus is useful in connection with so-called reverse-pull extra-oral traction procedures in which traction is applied to a patient's teeth in the anterior or forward direction relative to the head.

The apparatus 1 comprises headgear, generally designated 5, and a relatively rigid chin cup 7 having a cup-shaped central section 9 conforming to the contour of the patient's chin and end sections 11 connected to the headgear 5. It further comprises an implement in the form of a wire arm 13 on the central section 9 of the chin cup extending up from the chin cup for attachment at its upper end, via suitable elastic bands 15, to an instrumentality or instrumentalities (not shown) associated with the teeth for applying traction to the teeth generally in the anterior or forward direction with respect to the head. As described more fully hereinafter, means, generally designated 17, mounts the arm 13 on the chin cup 7 for movement in the direction of its longitudinal axis to enable adjustment of the position of the upper end of the arm relative to the mouth, and for pivotal movement relative to the chin cup 7 to enable angular adjustment of the arm relative to the chin cup generally in side-to-side direction with respect to the head. Mounting means 17 further serves to secure the arm in different positions of its axial and angular adjustment, whereby traction force may be applied to the orthodontic instrumentality on the teeth in the direction necessary for the treatment of a particular orthodontic deficiency.

As shown in FIGS. 1 and 2, the headgear 5 is of the type described in my U.S. Pat. Nos. 3,571,930 and 3,572,329 and comprises an overhead strap 19 extending from one side of the patient's head over the top of the head to the other side of the head, and a back strap 21 extending around the back of the head pivotally secured at its forward ends to the lower ends of the overhead straps by a pair of buttons 23 at the sides of the head. An occipital strap 25 extending over the rear portion of the head in a front-to-rear central vertical plane of the head connects a central portion of the overhead strap 19 with a central portion of the back strap 21. A pair of side straps 27 of suitable elastic webbing material connects the headgear and the chin cup and applies an upwardly and rearwardly directed force on the chin cup 7 for holding it in snugly on the patient's chin. Each side strap 27 at its lower end is looped through a closed hook 29 connected to a respective end section 11 of the chin cup and is folded back and stitched to itself. The upper end of each side strap is looped through a closed hook 31 pivotally carried on a button 32 on the overhead strap 19 adjacent the respective end thereof, and is secured to itself by a cinchtype clamp 33 for adjusting the length of the strap to vary the force applied to the chin cup. As illustrated in FIG. 2, the straps 27 extend rearwardy and upwardly from the chin cup thus applying a force to the chin cup which pulls it back against the patient's chin and also tends to rotate it in a counterclockwise direction (as viewed in FIG. 2) for counterbalancing the force applied to the chin cup by the bands 15 which tends to rotate it in a clockwise direction.

Figure 3:
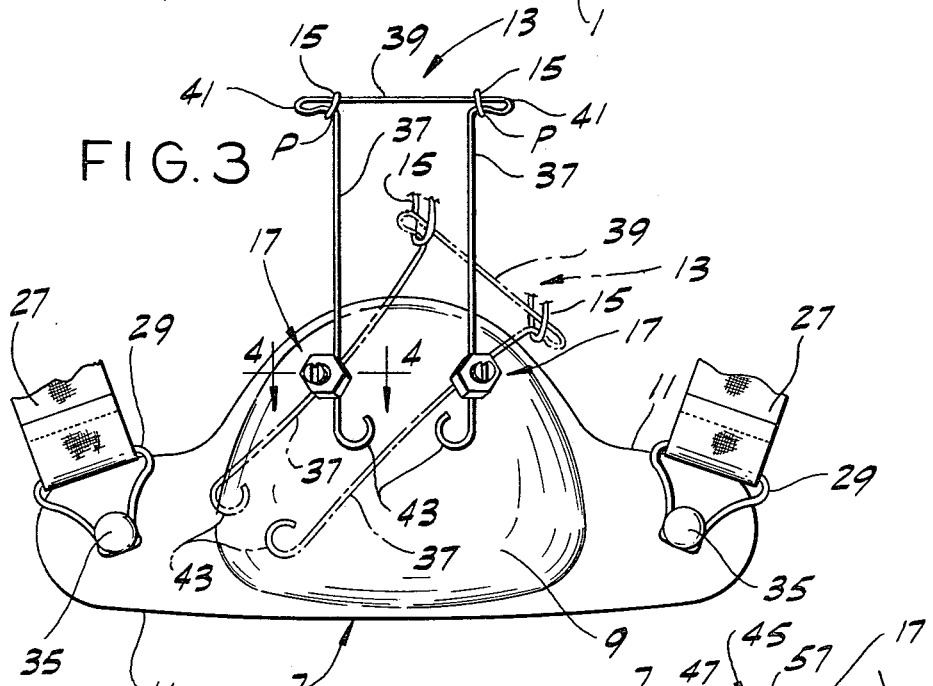
FIG. 3 is an enlarged front elevation of a chin cup of the orthodontic traction apparatus showing a wire arm on the chin cup, the wire arm being shown in solid lines in a raised position and in phantom in a lowered and inclined position.

The chin cup 7 is formed from a suitable thermoplastic material molded by a conventional molding process such as thermo-forming to have its end sections 11 integral with its central section 9. As best illustrated in FIG. 3, the end sections 11 project laterally from the sides of the central portion and carry a pair of buttons 35, one for each end section, to which are pivotally connected the closed hooks 29 of the headgear 5. The chin cup 7 at its outer or forward face has a layer of skin-colored fabric material giving the chin cup an aesthetically pleasing appearance, and at its inner or rearward face (not shown) has a layer of cushioning material such as a suitable fabric material enabling it comfortably to be worn for extended periods of time.

The wire arm 13 is formed from a single length of relatively stiff wire bent to have a pair of generally parallel side reaches 37, an upper reach 39 bridging the two side reaches, a pair of loops 41 at the junctures of the side and upper reaches, and a pair of hooks 43 at the lower ends of the side reaches. The side reaches 37 are slidably mounted on the chin cup for movement in the direction of their longitudinal axes by mounting means 17 in a manner described more fully hereinafter, with the loops 41 and the hooks 43 at the ends of the side reaches 37 functioning as stops to limit the range of axial movement. As best illustrated in FIG. 3, the elastic bands 15 are attached to the loops 41 at the upper end of the wire arm at a pair of attachment points P.

Mounting means 17 comprises a pair of pivot members constituted by studs 45 having heads 47 engageable with the inside surface of the chin cup and threaded shanks 49 projecting forwardly through a pair of holes 51 in the chin cup, and a pair of nuts 53 threaded on the shanks on the outside of the chin cup. The heads 47 of the studs are relatively thin and flat so as not to be uncomfortable to the patient. As shown, the studs 45 are disposed at approximately the same elevation on opposite sides of the central vertical front-to-back plane through the chin cup. The studs 45 are rotatable in holes 51 relative to the chin cup.

Figure 4:
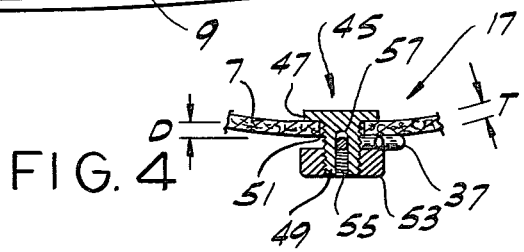
FIG. 4 is an enlarged horizontal section on line 4—4 of FIG. 3.

The shank 49 of each stud is of split construction, having an axial slot 55 therein extending from the forward end of the shank rearwardly (or inwardly) to a point 57 spaced a distance, designated D, from the forward face of the head 47 of the stud. As shown in FIG. 4, the slot 55 is of a width slightly greater than the diameter of the respective side reach 37 of the wire arm for slidably receiving the side reach. The pair of studs 45 thus mount the wire arm 13 on the chin cup for movement in the direction of its longitudinal axis relative to the chin cup 9 and for pivotal movement relative to the chin cup generally in side-to-side direction with respect to the head. This enables adjustment of the vertical and angular position of the arm 13 (and thus the location of the points of attachment P for the elastic bands 15) relative to the patient's mouth. For example, as shown in solid lines in FIG. 3, the arm may be adjusted to a raised position in which its upper reach 39 and the attachment points P are disposed generally horizontally well above the top of the chin cup 7 at the front of the mouth, or, as shown in phantom, to a lowered position in which the upper reach and the attachment points P are adjacent the top of the chin cup 9 and lie in an inclined plane at one side of the mouth.

As shown in FIG. 4, the distance D between the inner end 57 of the slot and the forward face of the head 47 of each stud 45 is less than the thickness, designated T, of the chin cup 7. Upon tightening the nuts 53 on the shanks 49 of the studs, the nuts thus serve to hold the side reaches 37 of the arm tightly pressed against the outer surface of the chin cup for selectively securing the arm 13 in different positions of axial and angular adjustment.

In the use of the orthodontic traction apparatus 1 of this invention, the apparatus is fitted on the patient's head in the position shown in FIGS. 1 and 2, with the overhead strap 19 extending over the top of the patient's head, the back strap 21 extending around the back of the head, the occipital strap 25 extending over the back portion of the head, the chin cup 7 on the chin, and the adjustable elastic straps 27 connecting the chin cup to the headgear. The cinch-type clamps 33 are adjusted to snug the chin cup up against the chin of the patient to hold it in relatively fixed position on the chin. With the nuts 53 spaced from the side reaches 37 of the arm 13, the axial and angular position of the arm 13 is adjusted to move the points of attachment P to the desired positions relative to the mouth, and the nuts are tightened to secure the arm in place. The elastic bands 15 are then connected to the loops 41 of the wire arm and to the orthodontic instrumentality (not shown) on the teeth for applying anteriorly-directed traction to the teeth in the desired direction.

The adjustability of the apparatus 1 enables the apparatus to be used for treatment of a number of different orthodontic deficiencies requiring the application of traction along different lines of action, thereby eliminating the need for orthodontic traction apparatus specially designed for each of these different deficiencies. Moreover, the apparatus is readily adjustable during the course of treatment to vary the direction at which traction force is applied to the teeth, should this be necessary.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Orthodontic traction apparatus adapted for attachment, via elastic bands or the like, to an instrumentality or instrumentalities associated with the teeth for applying traction to the teeth generally in the forward direction with respect to the head, comprising:
- headgear adapted to be worn on the head;
- a relatively rigid chin cup having central section shaped to conform to the contour of the chin and end sections adapted for connection to said headgear;
- an implement in the form of a wire arm on the central section of the chin cup adapted to extend up from the chin cup for attachment at its upper end, via said elastic bands, to said instrumentality or instrumentalities associated with the teeth for applying traction to the teeth generally in said forward direction;
- means mounting the arm on the central section of the chin cup for movement relative to the chin cup in the direction of the longitudinal axis of the arm for adjustment of the position of the upper end of the arm relative to the chin cup and to the mouth and for movement relative to the chin cup generally in side-to-side direction with respect to the head; and
- means for securing the arm in various positions of adjustment.

2. Orthodontic traction apparatus adapted for attachment, via elastic bands or the like, to an instrumentality or instrumentalities associated with the teeth for applying traction to the teeth generally in the forward direction with respect to the head, comprising:
- headgear adapted to be worn on the head;
- a relatively rigid chin cup having a central section shaped to conform to the contour of the chin and end sections adapted for connection to said headgear;
- an implement in the form of a wire arm on the central section of the chin cup adapted to extend up from the chin cup for attachment at its upper end, via said elastic bands, to said instrumentality or instrumentalities associated with the teeth for applying traction to the teeth generally in said forward direction;
- means mounting the arm for movement in the direction of its longitudinal axis for adjustment of the position of the upper end of the arm relative to the mouth and for movement relative to the chin cup generally in side-to-side direction with respect to the head; and
- means for securing the arm in various positions of adjustment,
- said mounting means being rotatably mounted on the chin cup for enabling angular adjustment of said arm relative to the chin cup, said securing means being adapted to secure the arm in various positions of axial and angular adjustment relative to the chin cup.

3. Apparatus as set forth in claim 2 wherein said arm comprises a length of wire bent to form a pair of generally parallel reaches extending up from the chin cup and a reach bridging the two parallel reaches at the upper ends thereof.

4. Apparatus as set forth in claim 3 wherein said mounting means comprises a pair of pivot members on the central section of the chin cup spaced generally longitudinally of the chin cup and having openings therein slidably receiving said parallel reaches of the wire arm for axial adjustment of the parallel reaches, and thus the arm, relative to the chin cup, said pivot members being pivotable about generally parallel axes extending in generally front-to-back direction with respect to the head.

5. Apparatus as set forth in claim 4 wherein said pivot members are constituted by a pair of studs having threaded shanks projecting forward from the chin cup, said shanks having said openings therein for receiving said parallel reaches of the wire arm, said securing means comprising nuts threaded on the shanks of the two studs for clamping the parallel reaches of the wire arm against the outside surface of the chin cup.

6. Apparatus as set forth in claim 5 wherein said shank openings are constituted by slots extending from the outer ends of the shanks inwardly along the axes of the shanks.

7. Apparatus as set forth in claim 6 wherein said end sections of the chin cup are integrally formed with the central section of the cup, each end section having a button thereon for connecting the chin cup to said headgear.

8. Apparatus as set forth in claim 7 wherein said chin cup is formed of a thermoformable sheet material molded to cup-shape.

9. Orthodontic traction apparatus adapted for attachment, via elastic bands or the like, to an instrumentality or instrumentalities associated with the teeth for applying traction to the teeth generally in the forward direction with respect to the head, comprising:
- headgear adapted to be worn on the head;
- a relatively rigid chin cup having a central section shaped to conform to the contour of the chin and end sections adapted for connection to the headgear;
- an implement in the form of a wire arm on the central section of the chin cup comprising a length of wire bent to have a pair of generally parallel reaches adapted to extend up from the chin cup at the front of the mouth and a reach bridging the two parallel reaches at the upper ends thereof, said bridging reach being adapted for attachment, via said elastic bands, to said instrumentality or instrumentalities associated with the teeth for applying traction to the teeth generally in said forward direction;
- means mounting the parallel reaches of the wire arm for sliding movement in the direction of the longitudinal axes of the reaches for adjustment of the position of the bridging reach of the wire arm relative to the mouth;
- said mounting means being mounted on the chin cup for angular adjustment of the arm relative to the chin cup generally in side-to-side direction with respect to the head; and
- means for securing the arm in various positions of axial and angular adjustment relative to the chin cup.

10. Apparatus as set forth in claim 9 wherein said mounting means comprises a pair of pivot members on the central section of the chin cup spaced generally longitudinally of the chin cup and having openings therein slidably receiving said parallel reaches of the wire arm for axial adjustment of the parallel reaches, and thus the arm, relative to the chin cup, said pivot members being pivotally mounted in the chin cup for pivoting on generally parallel axes extending in generally front-to-back direction with respect to the head.

11. Apparatus as set forth in claim 10 wherein said pivot members are constituted by a pair of studs having threaded shanks projecting forward from the chin cup, said shanks having said openings therein for receiving said parallel reaches of the wire arm, said securing means comprising nuts threaded on the shanks of the two studs for clamping the parallel reaches of the wire arm against the outside surface of the chin cup.

12. Apparatus as set forth in claim 11 wherein said shank openings are constituted by slots extending from the outer ends of the shanks inwardly along the axes of the shanks.

* * * * *